(12) United States Patent
Kim et al.

(10) Patent No.: US 11,422,077 B2
(45) Date of Patent: Aug. 23, 2022

(54) DEVICE FOR TESTING DURABILITY OF COWL CROSSBAR

(71) Applicant: Sewon Precision Industry Co., Ltd., Daegu (KR)

(72) Inventors: Moon Ki Kim, Daegu (KR); Sang Hyun Kim, Daegu (KR)

(*) Notice: Subject to any disclaimer, the term of this patent is extended or adjusted under 35 U.S.C. 154(b) by 284 days.

(21) Appl. No.: 16/833,515

(22) Filed: Mar. 28, 2020

(65) Prior Publication Data

US 2021/0302291 A1 Sep. 30, 2021

(51) Int. Cl.
| | | |
|---|---|---|
| *G01N 33/00* | (2006.01) | |
| *G01N 3/26* | (2006.01) | |
| *G01N 3/28* | (2006.01) | |
| *G01N 3/22* | (2006.01) | |
| *G01N 3/02* | (2006.01) | |
| *G01N 3/20* | (2006.01) | |

(52) U.S. Cl.
CPC ............. *G01N 3/22* (2013.01); *G01N 3/02* (2013.01); *G01N 3/20* (2013.01); *G01N 2033/0083* (2013.01)

(58) Field of Classification Search
CPC .. G01N 3/26; G01N 3/22; G01N 3/62; G01N 3/02; G01N 3/20; G01N 3/08; G01N 19/00; G01N 3/34; G01N 3/24; G01N 3/04; G01M 17/065; G01M 13/021; G01M 17/007; G01M 17/00; G01M 17/06; G01M 17/021; G01M 17/02; G01M 17/10; G01M 17/0078; G01M 17/0074; G01M 17/0072; G01M 13/04; G01M 7/08; G01M 13/02; G01M 13/00; G01M 13/027; G01L 5/0042; A61G 5/047; G09B 23/30

See application file for complete search history.

(56) References Cited

FOREIGN PATENT DOCUMENTS

| KR | 10-1997-0048097 | 7/1997 | | |
|---|---|---|---|---|
| KR | 10-2001-0008651 | 2/2001 | | |
| KR | 10-2004-0006580 | 1/2004 | | |
| KR | 20-0403426 | 12/2005 | | |
| KR | 100949449 B1 | * 3/2010 | ............... | B21J 9/06 |
| KR | 20130014145 A | * 7/2013 | ............... | B21C 1/24 |

OTHER PUBLICATIONS

English Specification of 10-1997-0048097.
English Specification of 10-2001-0008651.
English Specification of 10-2004-0006580
English Specification of 20-0403426.

* cited by examiner

*Primary Examiner* — Brandi N Hopkins
(74) *Attorney, Agent, or Firm* — Antonio Ha & U.S. Patent, LLC

(57) ABSTRACT

A device for testing durability of a cowl crossbar comprises a main picture including an input driver for a rotational durability test and a bending stiffness test on a specimen including motor driven power steering (MDPS)-mounted cowl crossbar, an output loader performing, together with the input driver, the rotational durability test and the bending stiffness test and outputting a test value, and a specimen stand disposed between the input driver and the output loader to relocatably support the specimen, and a controller controlling the main picture for the rotational durability test and the bending stiffness test.

13 Claims, 15 Drawing Sheets

DEVICE FOR TESTING DURABILITY OF COWL CROSSBAR

TECHNICAL FIELD

Embodiments of the disclosure relate to a device for testing the durability of a cowl crossbar, and more specifically, to a device for testing the durability of a cowl crossbar, which is a kind of car part, against, e.g., weld breaks, damage, or twists.

DESCRIPTION OF RELATED ART

The motor driven power steering (MDPS) system adopts an electric motor unlike the conventional hydraulic power steering system.

That is, in the MDPS system, the steering wheel is operated by an electric motor.

If the driver turns the steering wheel, a sensor detects the direction of turn and speed and enables the electric motor to rotate to transfer a proper driving force to the front wheels.

The MDPS system receives electricity from the vehicle power generator and, only when needed, operates the electric motor, thus saving fuel and reducing contaminant emissions.

Further, the MDPS system provides better fuel mileage, occupies a smaller space in the engine room, and weighs 5 kg or more less.

As such, the MDPS system is a major part of cars recently being launched and is continuously moved by the driver, and thus, its durability is critical for a long-term use.

Meanwhile, the MDPS system is typically mounted on the cowl crossbar and, thus, the durability of the cowl crossbar needs to be tested.

However, there is no proper one for those purposes, and a need arises for a device for testing the durability of cowl crossbars.

SUMMARY

According to an embodiment, there is provided a device for testing the durability of a cowl crossbar, which is a kind of car part, against, e.g., weld breaks, damage, or twists.

According to an embodiment, a device for testing durability of a cowl crossbar comprises a main picture including an input driver for a rotational durability test and a bending stiffness test on a specimen including motor driven power steering (MDPS)-mounted cowl crossbar, an output loader performing, together with the input driver, the rotational durability test and the bending stiffness test and outputting a test value, and a specimen stand disposed between the input driver and the output loader to relocatably support the specimen and a controller controlling the main picture for the rotational durability test and the bending stiffness test, wherein the input driver includes an input driver motor assembly forming an upper portion of the input driver and connected with the MDPS of the specimen and a steering wheel coupled with the MDPS to control an angle for the rotational durability test and a load for the bending stiffness test and an input driver frame supporting the input driver motor assembly, wherein the input driver, the output loader, and the specimen stand are altogether supported on a base frame.

For relocating relative to the specimen, the input driver is provided to be relocated by a first ball screw. The output loader is provided to be fixed in position by a U clamp, and wherein the specimen stand is provided to have its height adjusted depending on a position of installation of the specimen.

A plurality of installation through holes are formed in the base frame to install the input driver, the output loader, and the specimen stand, and wherein the input driver, the output loader, and the specimen stand are installed in predetermined positions on the base frame via the plurality of installation through holes.

A plurality of anti-slip feet are provided under the base frame, and wherein a cut is formed in a side of the base frame.

The input driver motor assembly is provided to have its height adjusted by a first screw jack, to be moved forward or backward by a second ball screw, and to have its angle adjusted by a second screw jack.

A first protractor is disposed around the second ball screw and the second screw jack.

The input driver motor assembly includes a first servomotor for the rotational durability test, a first air cylinder for the bending stiffness test, a first position detecting module capable of grasping a position of the first air cylinder, a first load cell capable of measuring an input load, a wheel clamp clamped to or unclamped from the steering wheel; and a clamp bar connected with the wheel clamp and the first air cylinder.

A connector is provided to connect the MDPS to a first serration while controlling an angle of the MDPS by power transferred from the first servomotor through a first decelerator, a first coupling, and a first torque cell to the first serration for the rotational durability test. The input driver frame includes a pneumatic line unit, and wherein the pneumatic line unit controls a load and direction of the first air cylinder using an air pressure.

The pneumatic line unit includes a direction turning valve supplying air to the first air cylinder and enabling moving forward or backward or stopping, an electronic regulator controlling a pressure of the air in a range from 0 Bar to 9 Bar; and a manual regulator setting an input air pressure to 6 Bar.

The output loader includes an output loader motor assembly connected with the MDPS to provide a load. The output loader motor assembly includes a second servomotor for the rotational durability test, and wherein upon the rotational durability test, when a second serration connected with the MDPS is rotated, the second servomotor provides a load in an opposite direction, and the load is measured by a second torque cell between the second serration and the second servomotor and output in a graph.

The specimen stand includes a T slot table on which the specimen is mounted, a stand screw jack adjusting a height of the T slot table, a plurality of specimen supporting jigs provided on the T slot table and supporting the specimen, a first side support and a second side support, together with the specimen supporting jigs, supporting the specimen, a specimen middle support provided between the first side support and the second side support, an upper jig disposed at an upper end of the specimen middle support and supporting the specimen; and a plurality of bottom jigs arranged around the specimen middle support and supporting the specimen.

The device further comprises an error lamp controlled by the controller to visually output an error in a process of testing the durability of the cowl crossbar; and an error buzzer controlled to be operated together with the error lamp by the controller and audibly outputting the error.

The device further comprises a power stopping device operated in association with the controller. The controller controls the power stopping device to automatically stop power when controlling to provide a notification signal to the error lamp and the error buzzer.

With the above-described structure and operation, embodiments of the disclosure enables pre-check or verification on the durability of an MDPS-mounted cowl crossbar against weld breaks, damage, or twists, in such a manner as to forcedly or steadily apply, e.g., vibration or handle movement, thus providing better reliability on the resultant values. Further, embodiments of the disclosure allow for reverse analysis on any issues, thus reducing loss via pre-detection on issues.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF EXEMPLARY EMBODIMENTS

Figure 1:
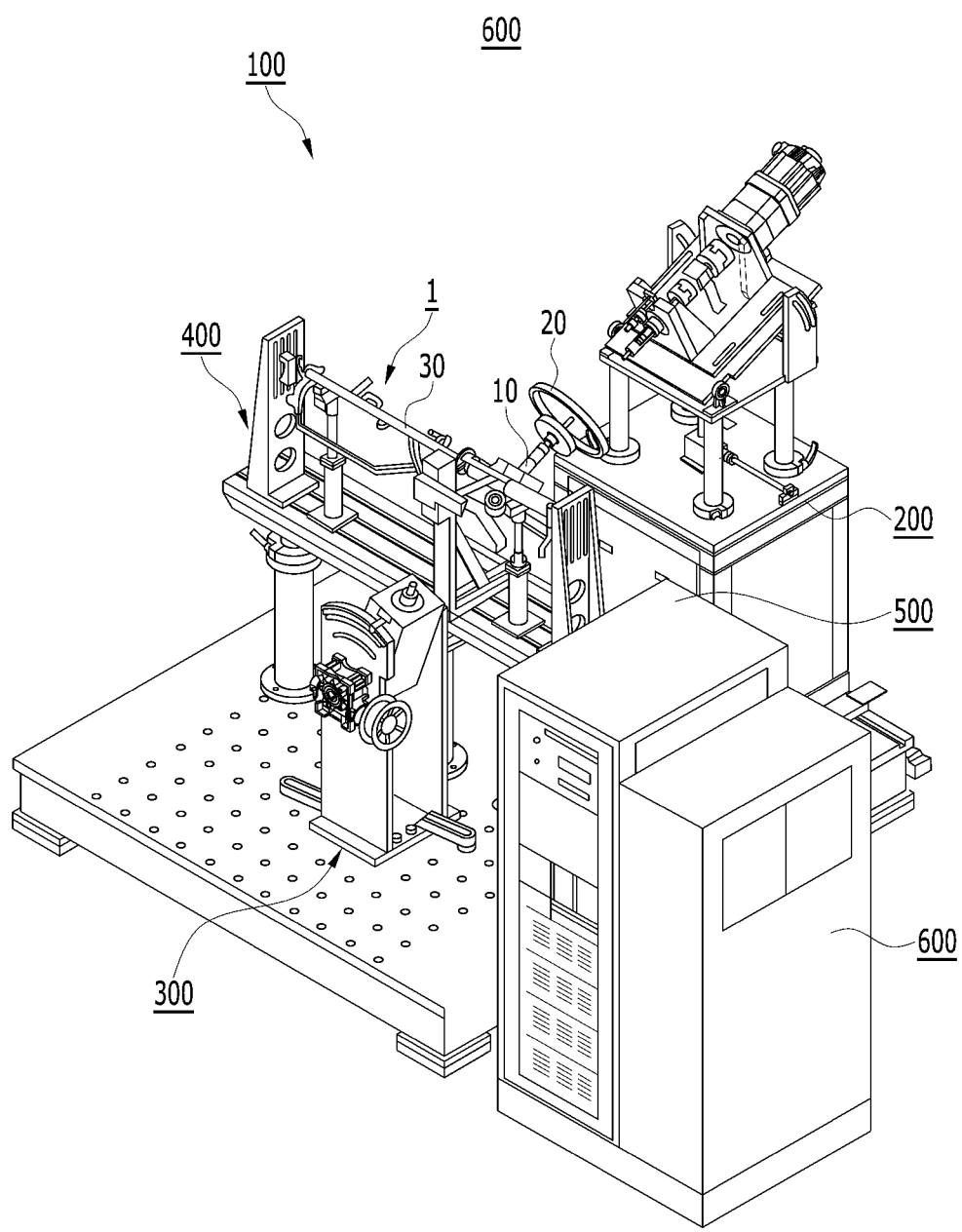
FIG. 1 is a view illustrating a configuration of a device for testing the durability of a cowl crossbar according to an embodiment.

Advantages and features of the present disclosure, and methods for achieving the same may be understood through the embodiments to be described below taken in conjunction with the accompanying drawings.

However, the scope of the disclosure is not limited to embodiments described herein, but rather, other various changes may be made thereto.

However, the present disclosure is not limited to the embodiments disclosed herein, and various changes may be made thereto. The embodiments disclosed herein are provided only to inform one of ordinary skilled in the art of the category of the present disclosure. The present disclosure is defined only by the appended claims.

The scope of the disclosure is defined by the appended claims.

In some embodiments, known components, operations, and techniques are not described in detail to avoid the disclosure from ambiguity in interpretation.

The same reference numeral denotes the same element throughout the specification.

The terms as used herein are provided merely to describe some embodiments thereof, but not intended as limiting the present disclosure.

As used herein, the singular forms "a," "an," and "the" are intended to include the plural forms as well, unless the context clearly indicates otherwise.

As used herein, the term "comprises" and/or "comprising" does not exclude the presence or addition of one or more other components, steps, operations, and/or elements than the component, step, operation, and/or element already mentioned.

Unless defined otherwise, all the terms (including technical and scientific terms) used herein may be construed as commonly appreciated by one of ordinary skill in the art to which the present disclosure pertains.

Further, terms defined in a dictionary commonly used are not ideally or overly interpreted unless defined expressly or specifically.

Hereinafter, embodiments of the present disclosure are described in detail with reference to the accompanying drawings.

Figure 2:
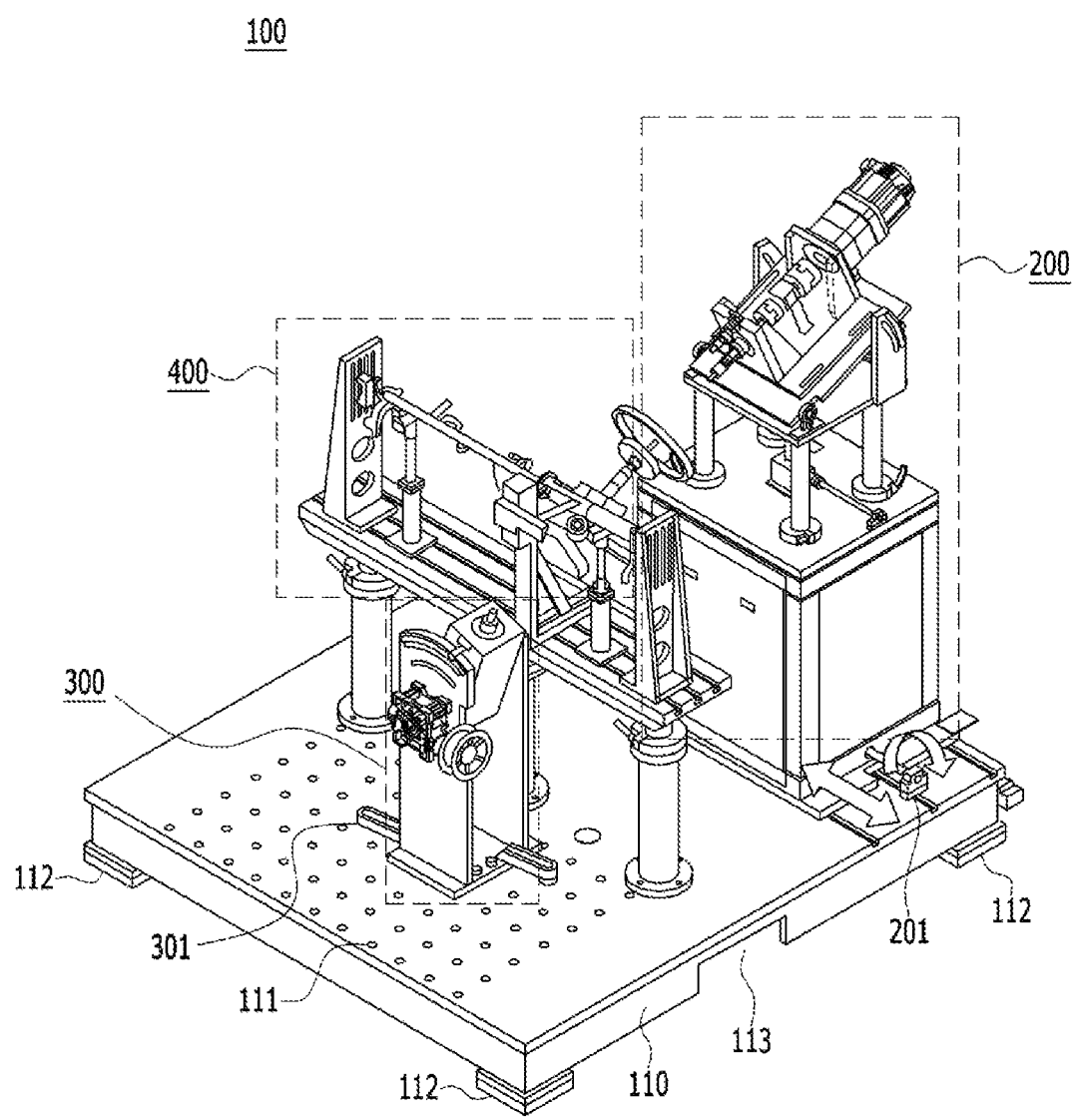
FIG. 2 is an enlarged view illustrating a main picture as shown in FIG. 1.
Figure 3:
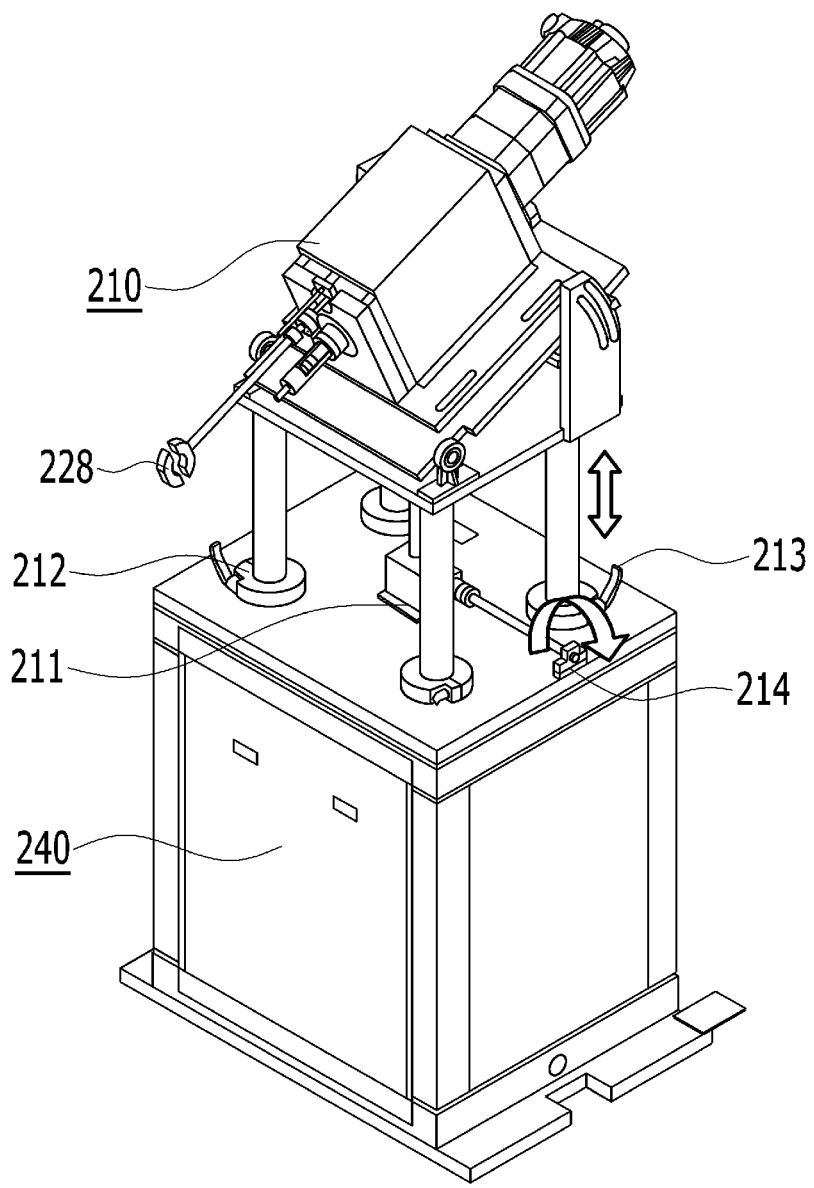
FIG. 3 is an enlarged view illustrating an input driver.
Figure 4:
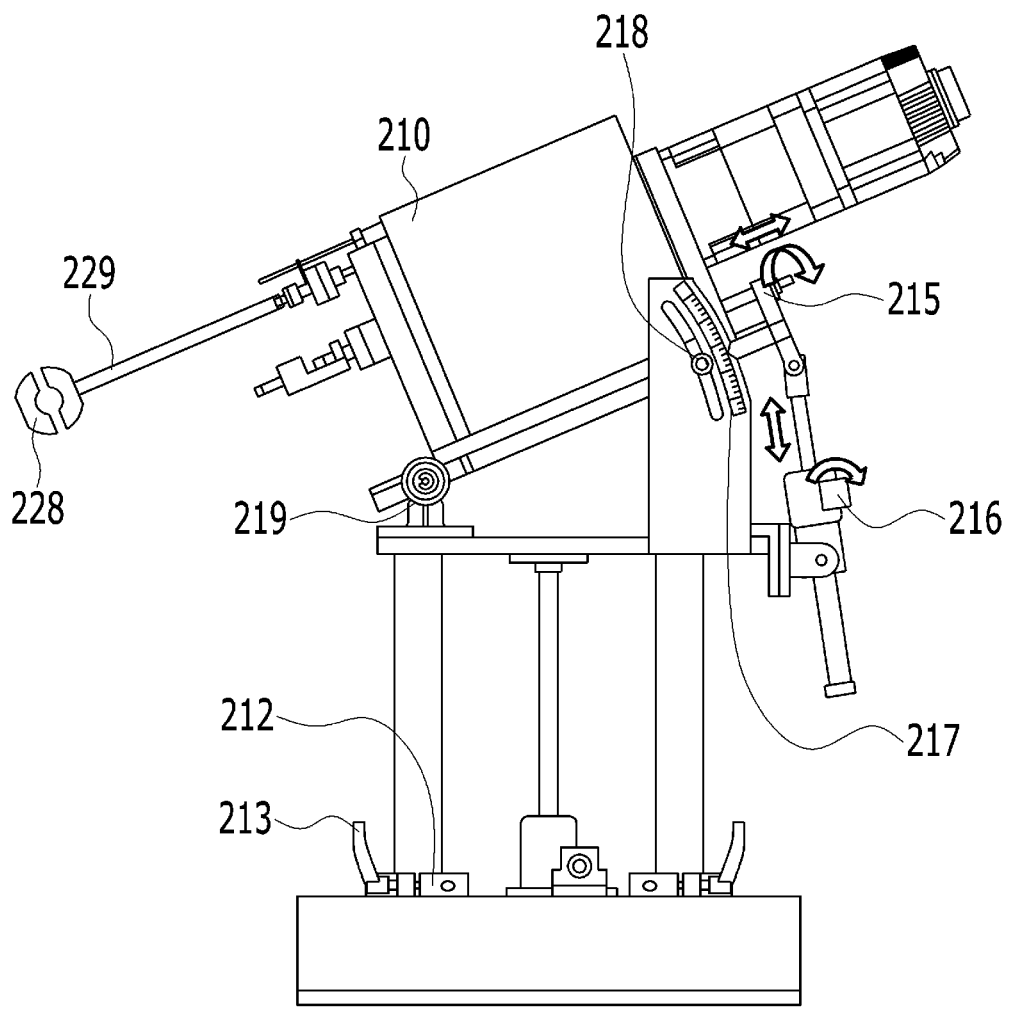
FIG. 4 is an enlarged side view illustrating a major portion of FIG. 3.
Figure 5:
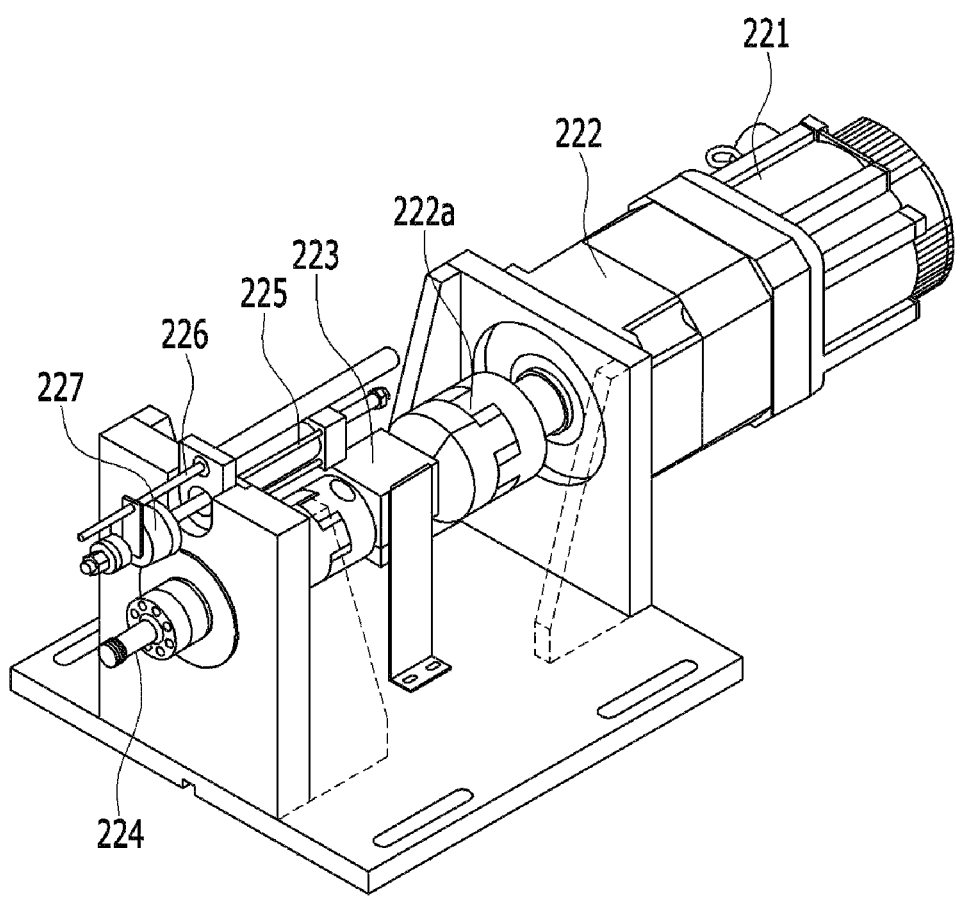
FIG. 5 is a view illustrating a detailed structure of an input driver motor assembly.
Figure 6:
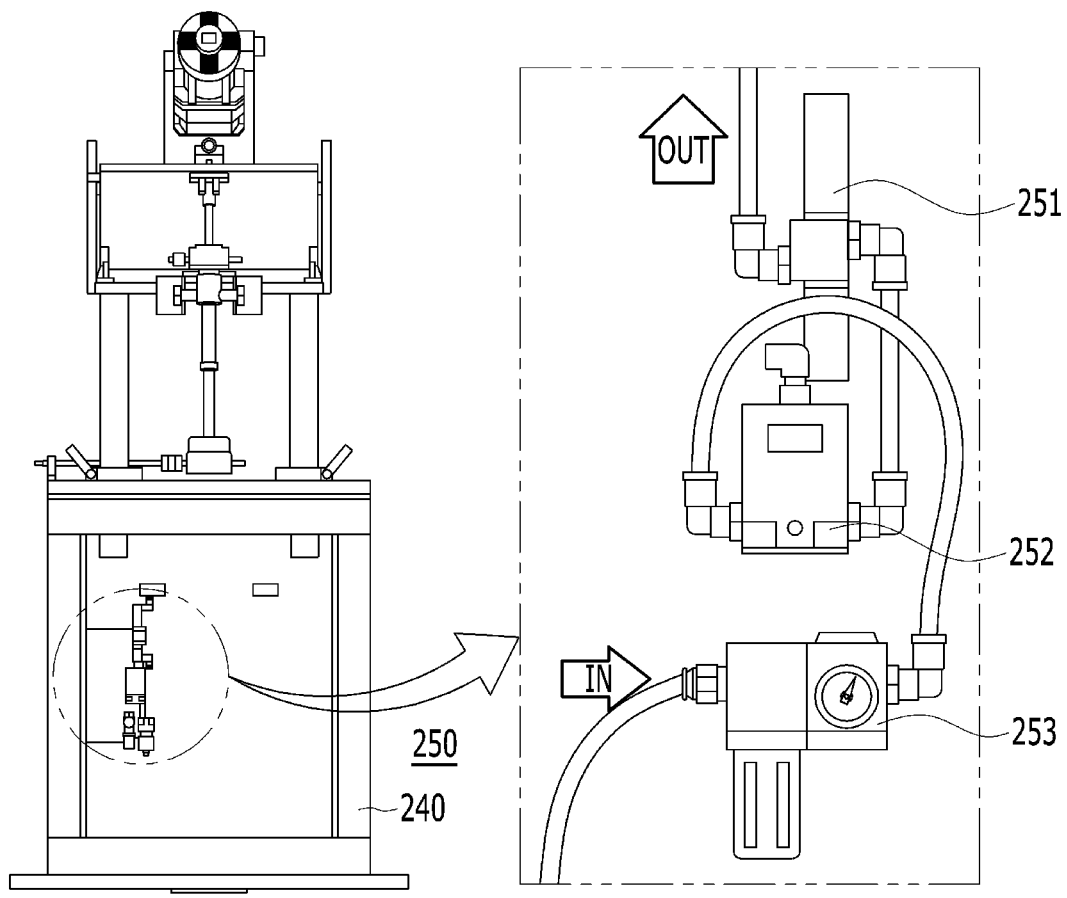
FIG. 6 is a view illustrating a pneumatic line unit provided in an input driver frame.
Figure 7:
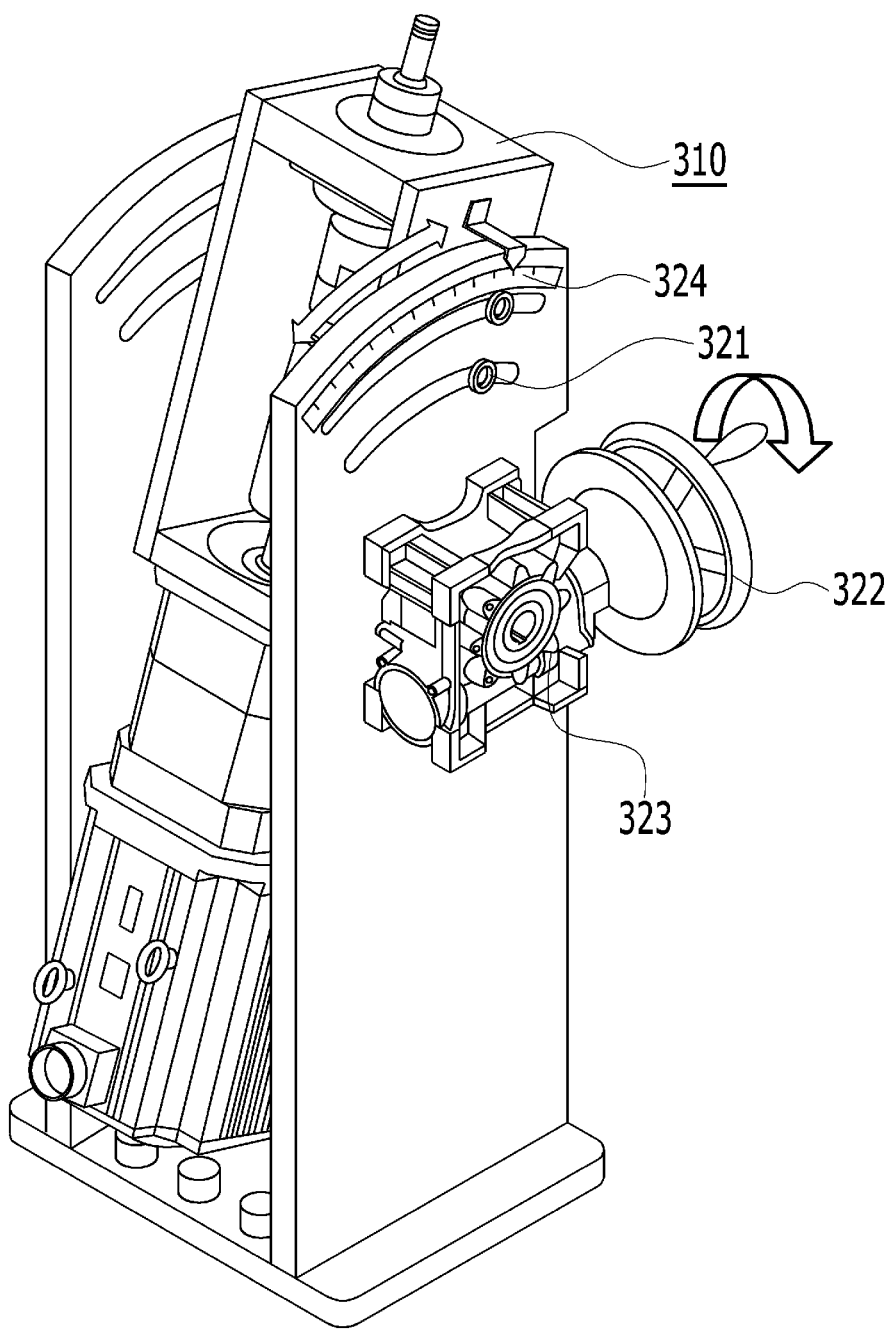
FIG. 7 is an enlarged view illustrating an output loader.
Figure 8:
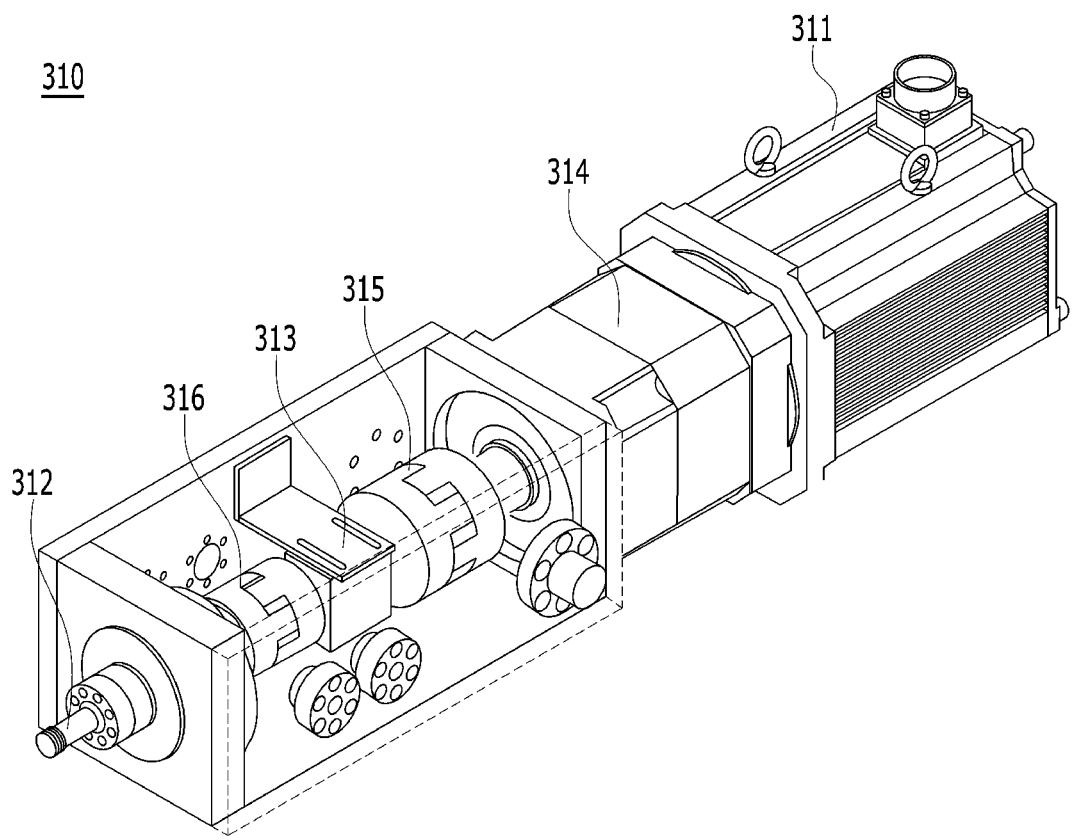
FIG. 8 is a view illustrating a detailed structure of an output loader motor assembly.
Figure 9:
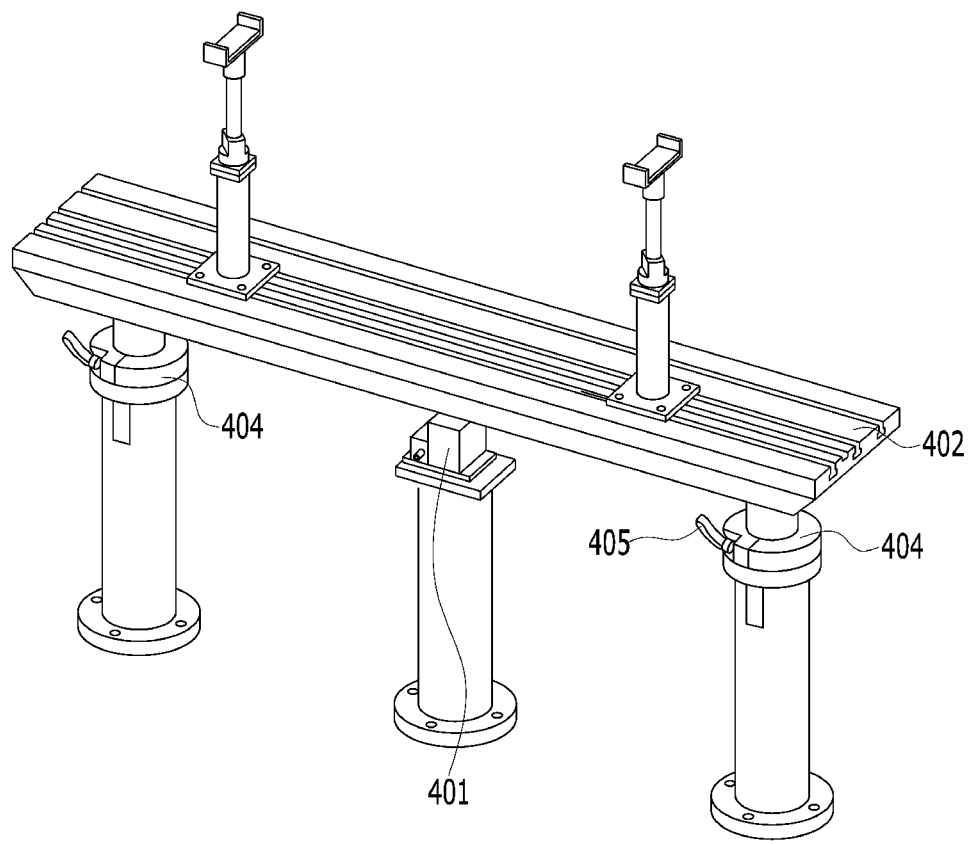
FIG. 9 is an enlarged view illustrating a specimen stand.
Figure 10:
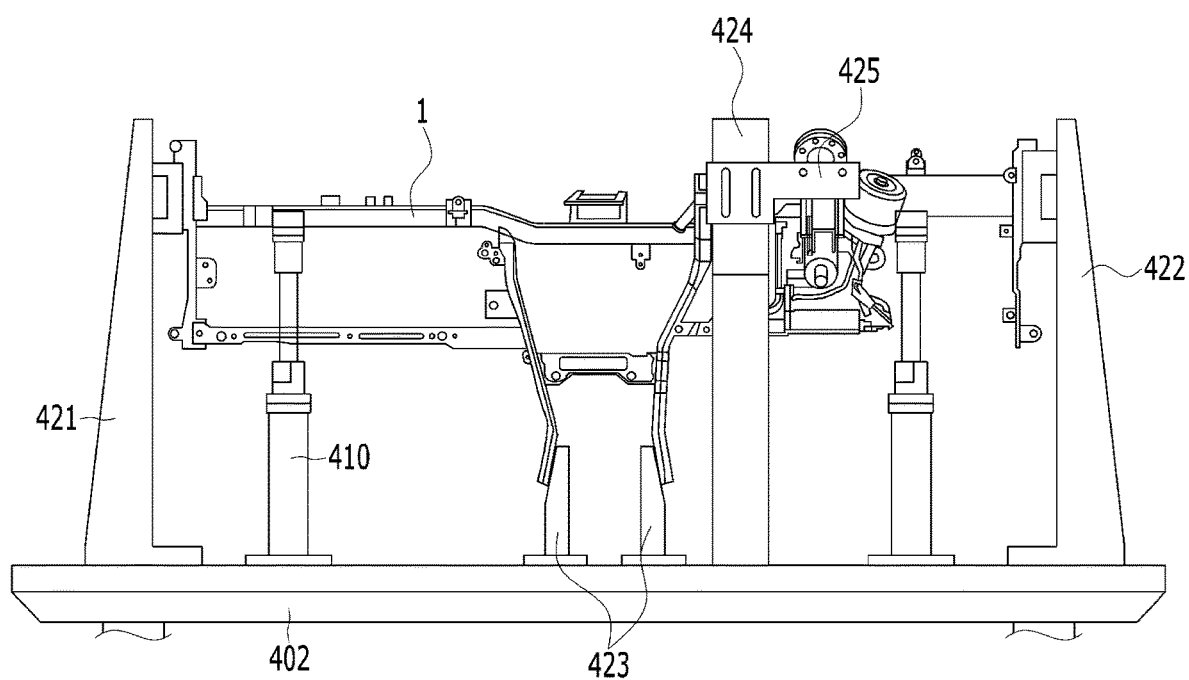
FIG. 10 is a side view illustrating an example in which a specimen is clamped to a specimen stand.
Figure 11:
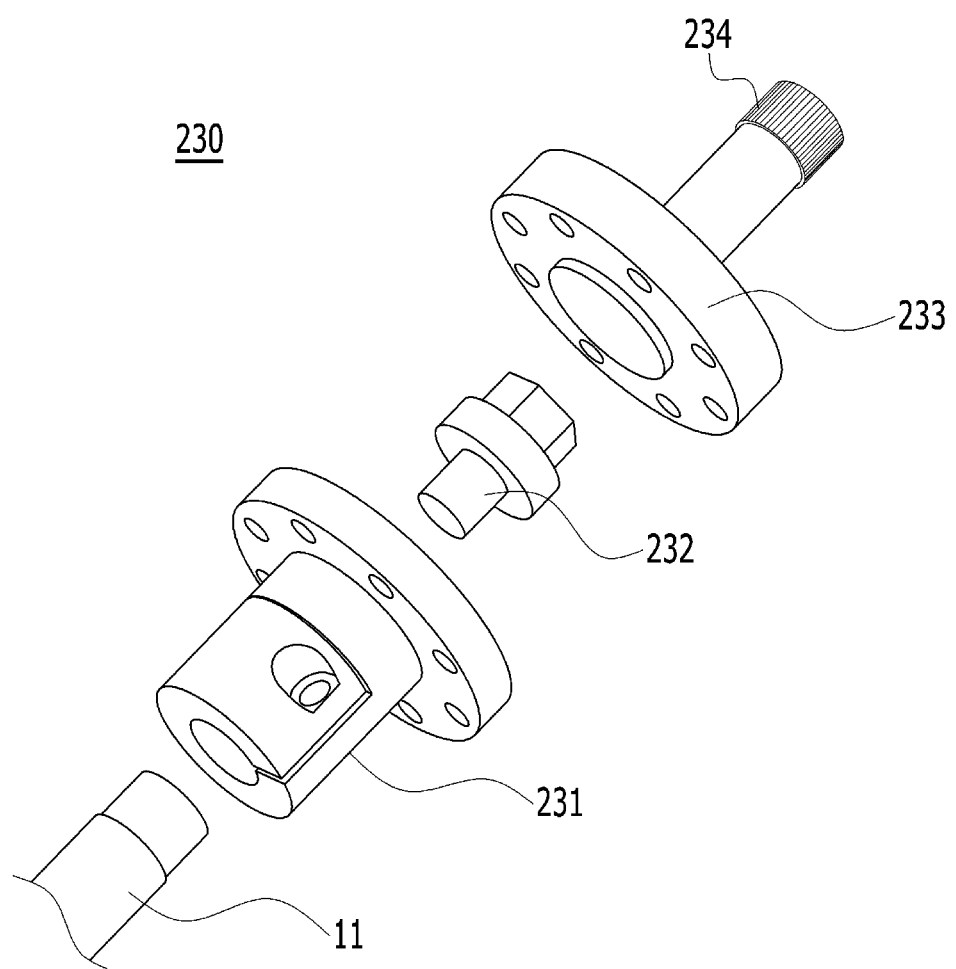
FIG. 11 is a view illustrating a structure of a connector for a rotational durability test.
Figure 12:
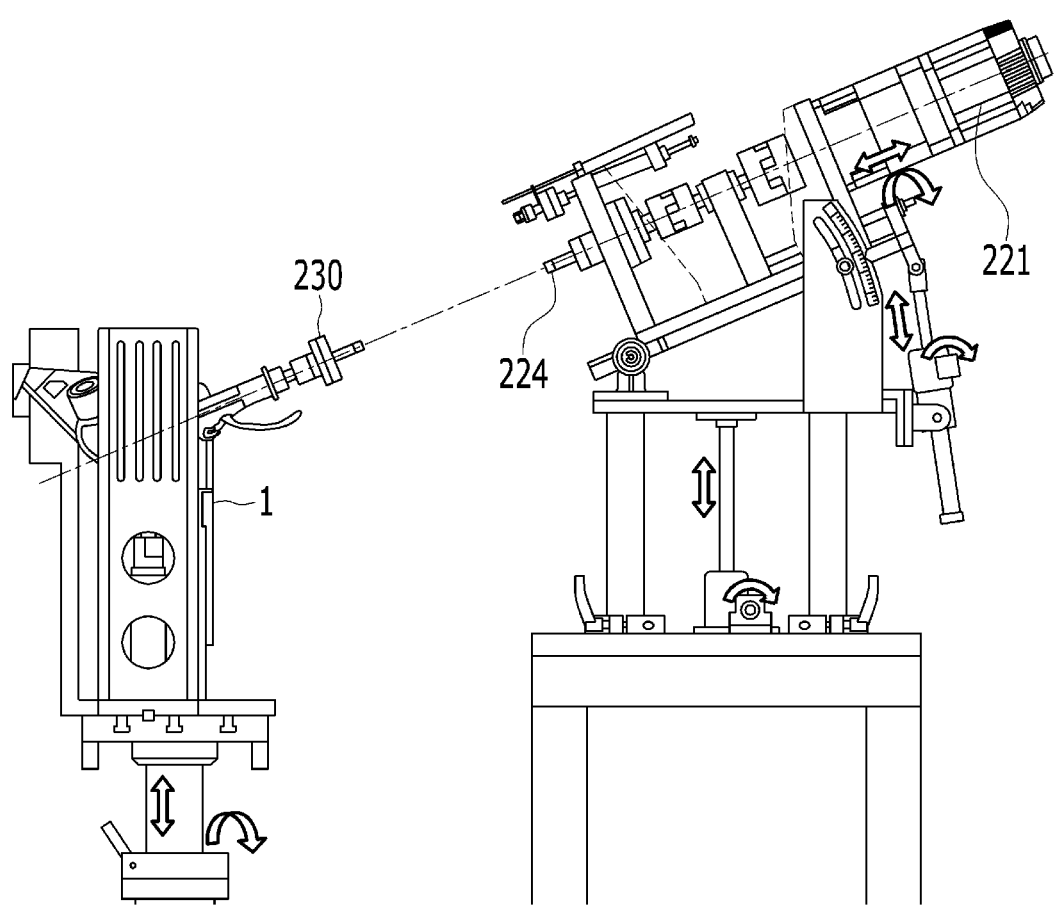
FIG. 12 is a layout view for a rotational durability test.
Figure 13:
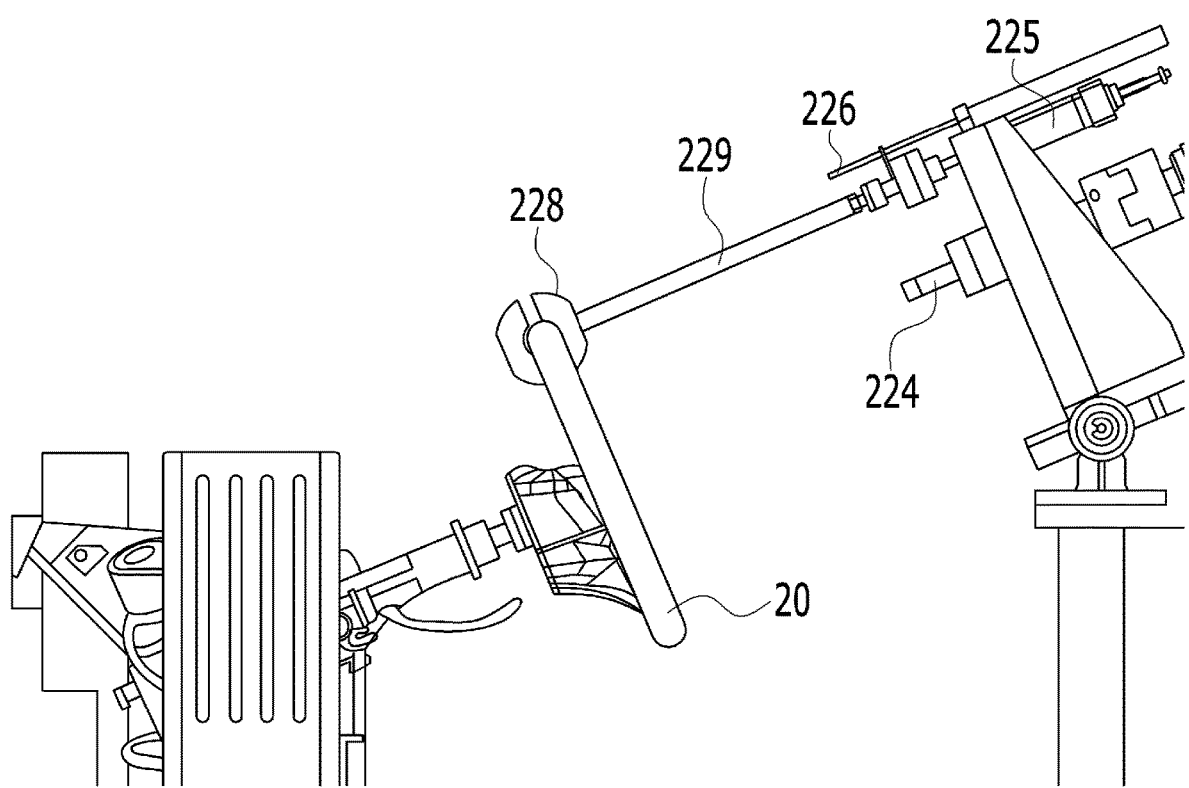
FIG. 13 is a layout view for a bending stiffness test.
Figure 14:
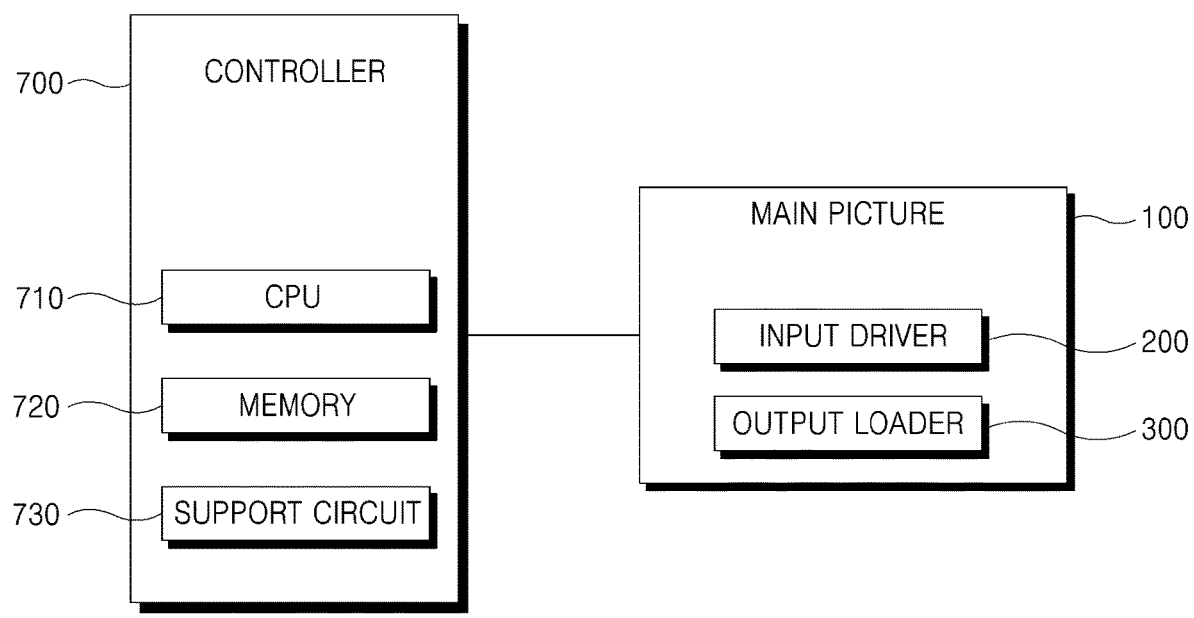
FIG. 14 is a block diagram illustrating an example of controlling a device for testing the durability of a cowl crossbar according to an embodiment.

FIG. 1 is a view illustrating a configuration of a device for testing the durability of a cowl crossbar according to an embodiment. FIG. 2 is an enlarged view illustrating a main picture as shown in FIG. 1. FIG. 3 is an enlarged view illustrating an input driver. FIG. 4 is an enlarged side view illustrating a major portion of FIG. 3. FIG. 5 is a view illustrating a detailed structure of an input driver motor assembly. FIG. 6 is a view illustrating a pneumatic line unit provided in an input driver frame. FIG. 7 is an enlarged view illustrating an output loader. FIG. 8 is a view illustrating a detailed structure of an output loader motor assembly. FIG. 9 is an enlarged view illustrating a specimen stand. FIG. 10 is a side view illustrating an example in which a specimen is clamped to a specimen stand. FIG. 11 is a view illustrating a structure of a connector for a rotational durability test. FIG. 12 is a layout view for a rotational durability test. FIG. 13 is a layout view for a bending stiffness test. FIG. 14 is a block diagram illustrating an example of controlling a device for testing the durability of a cowl crossbar according to an embodiment.

According to an embodiment, a device for testing the durability of a cowl crossbar enables pre-check or verification on the durability of an MDPS-mounted cowl crossbar against weld breaks, damage, or twists, in such a manner as to forcedly or steadily apply, e.g., vibration or handle movement, thus providing better reliability on the resultant values. Further, embodiments of the disclosure allow for reverse analysis on any issues, thus reducing loss via pre-detection on issues.

In particular, according to an embodiment, a device for testing the durability of a cowl crossbar may perform a rotational durability test on a MDPS-mounted cowl crossbar 30 as shown in FIG. 12 and a bending stiffness test on the MDPS-mounted cowl crossbar 30 as shown in FIG. 13.

Referring to FIG. 1, according to an embodiment, a device for testing the durability of a cowl crossbar may include a main picture 100, a rack 500, and an electronic box 600.

A controller 700 for controlling the rotational durability test and bending stiffness test may be equipped in the rack 500 and the electronic box 600.

As set forth above, a motor driven power steering (MDPS) 10 and a steering wheel 20 may be mounted on the cowl crossbar 30.

The cowl crossbar 30 and the MDPS 10 and the steering wheel 20 mounted on the cowl crossbar 30 are collectively referred to as a specimen 1.

The steering wheel 20 is substantially circular regardless of car makers, but the MDPS 10 and the cowl crossbar 30 may differ in size, structure, and shape from maker to maker.

The scope of the disclosure is not limited to those shown in the drawings.

A piece of equipment for driving the device for testing the durability of a cowl crossbar has the following specifications: 240V, 3 P, and 145 A.

Further, an air pressure of 7 bar or more is needed.

However, the scope of the disclosure is not limited to the above conditions.

The main picture 100 may include an input driver 200, an output loader 300, and a specimen stand 400.

The input driver 200 is a device that performs a rotational durability test and bending stiffness test for the specimen 1.

The output loader 300 is a device that, along with the input driver 200, performs a rotational durability test and bending stiffness test, and that outputs the results of test.

The specimen stand 400 is a structure that is disposed between the input driver 200 and the output loader 300 and supports the specimen 1 in such a manner that the specimen 1 may be relocated.

The input driver 200, the output loader 300, and the specimen stand 400 may be supported together on a base frame 110.

Thus, the input driver 200, output loader 300, and the specimen stand 400 may be advantageously moved simultaneously.

A plurality of installation through holes 111 are formed in the base frame 110 to install the input driver 200, output loader 300, and specimen stand 400.

The input driver 200, output loader 300, and specimen stand 400 may be installed in proper positions on the base frame 110 via the plurality of through holes 111.

A plurality of anti-slip feet 112 are provided under the base frame 110.

The anti-slip feet 112 may be arranged in four corners of the base frame 110 to stably support the base frame 110.

A cut 113 may be formed in a side of the base frame 110.

To be relocated relative to the specimen 1, the input driver 200 may be moved left/right along the specimen 1 by a first ball screw 201.

The output loader 300 may be fastened to a U clamp 301 to fit the MDPS 10.

The specimen stand 400 may have its height adjusted depending on the position of installation of the specimen 1.

The input driver 200 performs a rotational durability test and bending stiffness test on the specimen 1.

The input driver 200 includes an input driver motor assembly 210 that forms an upper portion thereof and is connected with the MDPS 10 and steering wheel 20 of the specimen 1 to control an angle for a rotational durability test and a load for a bending stiffness test and an input driver frame 240 that forms a lower portion thereof and supports the input driver motor assembly 210.

The input driver motor assembly 210 may have its height adjusted using a first screw jack 211.

A method for adjusting the height of the input driver motor assembly 210 is described below.

First, four clamps 212 are loosened using clamp levers 213 attached to the clamps 212.

Then, the height of a screw jack shaft 214 is adjusted using a 10 mm spanner or 10 mm box wrench.

If the height adjustment is done, the four clamps 212 are tightened back.

The input driver motor assembly 210 may be rotated forward or backward by a second ball screw 215 and its angle may be adjusted by a second screw jack 216.

The angle may be adjusted in a range from 17 degrees to 30 degrees.

A first protractor 217 is disposed around the second ball screw 215 and the second screw jack 216.

A unit bearing 219 is provided opposite the second screw jack 216.

A method for adjusting the angle of the input driver motor assembly 210 is described below.

First, a fastening bolt 218 is loosened.

Then, the angle of the second screw jack 216 is adjusted using a 10 mm spanner or 10 mm box wrench.

The angle is adjusted while checking the first protractor 217, and then, the fastening bolt 218 is tightened back.

The input driver motor assembly 210 includes a first servomotor 221 for a rotational durability test and a first air cylinder 225 for a bending stiffness test.

For a rotational durability test, power form the first servomotor 221 is transferred through a first decelerator 222, a first coupling 222a, and first torque cell 223 to a first serration 224 to thereby control the angle of the MDPS 10.

For the MDPS 10 to connect to the first serration 224, a connector 230 in the structure shown in FIG. 11 is used.

The connector 230 may include a first connecting structure 231 connected to the shaft 11 of the MDPS 10, a second connecting structure 233 with a connection serration 234 connected to the first serration 224, and a connecting bolt 232 for connecting the first and second connecting structures 231 and 233.

A rotational durability test may be performed by rotation of the first servomotor 221, with the connector 230 connected with the MDPS 10, and then first serration 224 connected with the connection serration 234 of the second connecting structure 233, as shown in FIG. 12.

For a bending stiffness test, the first air cylinder 225 may be used. The bending stiffness test of the specimen 1 may be performed with a first position detection module (e.g., linear variable differential transformer (LVDT) 226 capable of grasping the position of the first air cylinder and a first load cell 227 capable of measuring the input load.

For such a bending stiffness test, there may be provided a wheel clamp 228 that may be clamped to or unclamped from the steering wheel 20 and a clamp bar 229 connected with the wheel clamp 228 and the first air cylinder 225, as shown in FIG. 4.

A bending stiffness test may be performed in such a manner as to clamp the wheel clamp 228 to the steering wheel 20 and then pressurize the clamp bar 229 using the first air cylinder 225 while detecting it with the first position detecting module (LVDT) 226 as shown in FIG. 13.

The input driver frame 240 includes a pneumatic line unit 250 as shown in FIG. 6.

The pneumatic line unit 250 is disposed behind the input driver frame 240 and controls the load and direction of the first air cylinder 225 using an air pressure.

The pneumatic line unit 250 includes a direction turning valve 251, an electronic regulator 252, and a manual regulator 253.

The direction turning valve 251 supplies air to the first air cylinder 225 and allows it to move forward, backward, or stop.

The electronic regulator 252 controls the air pressure in a range from 0 Bar to 9 Bar.

The manual regulator 253 adjusts the input air pressure to a predetermined level and supplies the air to the electronic regulator 252.

In other words, control is performed manually by turning a valve.

It may be set to 6 bar.

The output loader 300 includes an output loader motor assembly 310 connected with the MDPS 10 to give a load as shown in FIG. 7.

The angle of installation of the MDPS 10 is identified and adjusted via the output loader motor assembly 310.

A method for adjusting the angle of the output loader motor assembly 310 is described below.

First, the fastening bolt 321 is loosened.

Then, the angle of the output loader motor assembly 310 is adjusted by a handle 322.

At this time, the angle of the output loader motor assembly 310 is adjusted while checking a second protractor 324.

A handle decelerator 323 is connected to the handle 322.

If adjustment is done, the fastening bolt 321 is tightened and fastened back.

The output loader motor assembly 310 includes a second servomotor 311 for rotational durability testing.

Upon rotational durability testing, if the second serration 312 connected with the MDPS 10 is rotated, the second servomotor 311 gives a load in the opposite direction.

The load is measured by a second torque cell 313 between the second serration 312 and the second servomotor 311 and is shown in graph.

A second decelerator 314 is connected to the second servomotor 311.

The second decelerator 314 and the second torque cell 313 are connected together by a second coupling 315, and the second torque cell 313 and the second serration 312 are connected together by a second coupling 316.

The specimen stand 400 loads and fastens the specimen 1 as does it on an actual vehicle.

The height of a T slot table 402 on which the specimen 1 is mounted may be adjusted using a stand screw jack 401.

A plurality of specimen supporting jigs 410 are arranged on the T slot table 402 to support the specimen 1.

Shock absorbers may be applied to the jigs 410 for supporting the specimen 1.

A first side support 421 and a second side support 422 are provided to, together with the specimen supporting jigs 410, support the specimen 1.

The first and second side supports 421 and 422 laterally support the specimen 1, with their first sides fastened to the T slot table 402 and their second sides screwed with the specimen 1.

A specimen middle support 424 is provided between the first and second side supports 421 and 422.

An upper jig 425 is provided at an upper end of the specimen middle support 424 to fasten the specimen 1 and the specimen middle support 424 via a screw to thereby support the specimen 1 in the position.

A plurality of bottom jigs 423 are provided around the specimen middle support 424 to support the bottom of the specimen 1.

The bottom jigs 423 may also support the specimen 1 in a screw fastening manner.

A method for adjusting the height of the T slot table 402 is described below.

Stand clamps 404 are loosened using stand clamp levers 405 coupled to the stand clamps 404.

Then, the height of the T slot table 402 is adjusted using a 10 mm spanner or 10 mm box wrench on the stand screw jack 401.

If the height adjustment is done, the stand clamps 404 are tightened back.

As such, as the height of the T slot table 402 is adjusted, the specimen supporting jig 410 positioned thereover may also have its height adjusted and, resultantly, the height of the specimen 1 may also be adjusted.

Thus, various shapes of specimens may be tested.

Further, the controller 700 controls the rotational durability test and bending stiffness test on the specimen 1.

In other words, the controller 700 controls the operation of the main picture 100, in particular, the input driver 200 and the output loader 300, for the rotational durability test of FIG. 12 and the bending stiffness test of FIG. 13.

The controller 700 may include a central processing unit (CPU) 710, a memory 720, and a support circuit 730.

According to an embodiment, the CPU 710 may be one of various computer processors industrially applicable to control the operation of the main picture 100, in particular, the input driver 200 and the output loader 300, for the rotational durability test of FIG. 12 and the bending stiffness test of FIG. 13.

The memory 720 is connected with the central processing unit 710.

The memory 720 may be a computer-readable recording medium, installable locally or remotely, and may be at least one of, e.g., random access memories (RAMs), read-only memories (ROMs), floppy disks, hard disks, or any other various forms of digital storage.

The support circuit 730 may be coupled with the central processing unit 710 to support typical operations of the processor.

The support circuit 730 may include a cache, a power supply, a clock circuit, an input/output circuit, and a sub system.

Further, the controller 700 controls the rotational durability test and bending stiffness test on the specimen 1.

A series of processes in which the controller 700 controls the operation of the main picture 100, in particular, the input driver 200 and the output loader 300, for the rotational durability test of FIG. 12 and the bending stiffness test of FIG. 13 may be stored in the memory 720.

For example, software routines may be stored in the memory 720.

The software routines may be stored or executed by other central processing unit (not shown).

Although the processes are described to be executed by software routines, at least some of the processes according to an embodiment may be performed by hardware.

As such, the processes according to an embodiment may be implemented in software executed on a computer system, in hardware, e.g., an integrated circuit (IC), or in a combination of software and hardware.

With the above-described structure and operation, embodiments of the disclosure enables pre-check or verification on the durability of an MDPS-mounted cowl crossbar against weld breaks, damage, or twists, in such a manner as to forcedly or steadily apply, e.g., vibration or handle movement, thus providing better reliability on the resultant values. Further, embodiments of the disclosure allow for reverse analysis on any issues, thus reducing loss via pre-detection on issues.

Figure 15:
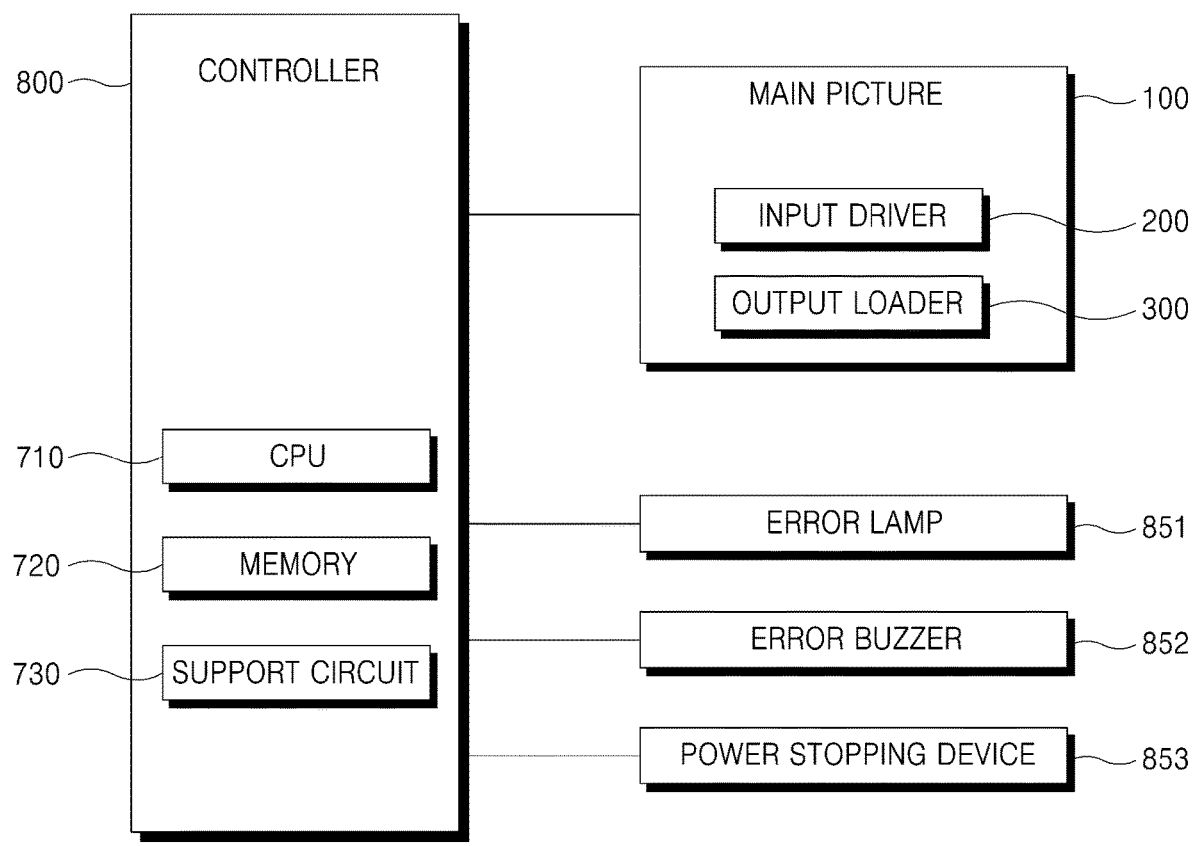
FIG. 15 is a block diagram illustrating an example of controlling a device for testing the durability of a cowl crossbar according to another embodiment.

FIG. 15 is a block diagram illustrating an example of controlling a device for testing the durability of a cowl crossbar according to another embodiment.

Referring to FIG. 15, the device for testing the durability of a cowl crossbar may have substantially the same structure as that described above.

According to an embodiment, the device for testing the durability of a cowl crossbar may further include an error lamp 851 and an error buzzer 852.

The error lamp 851 and the error buzzer 852 may be connected wiredly or wirelessly.

The error lamp 851 is a device controlled by the controller 800 to visually output an error in the process of testing the durability of a cowl crossbar.

There may be one or more error lamps 851.

The error lamp 851 allows the worker to visually identify and handle errors in the process of testing the durability of a cowl crossbar.

The error buzzer 852 is a device controlled by the controller 800 to be operated along with the error lamp 851 and to audibly output errors.

There may be one or more error buzzers 852.

The error buzzer 852 allows the worker to audibly identify and handle errors in the process of testing the durability of a cowl crossbar.

According to an embodiment, the device for testing the durability of a cowl crossbar may further include a power stopping device 853 operated in association with the controller 800.

The power stopping device 853 may be controlled by the controller 800 to cut off supply of power to the transfer pressing apparatus to stop the operation of the transfer pressing apparatus.

According to an embodiment, the controller 800 may simultaneously control the power stopping device 853 to automatically cut off power when controlling to provide a notification signal to the error lamp 851 and error buzzer 852.

Thus, unnecessary operations of the apparatus may be prevented.

Such a structure may also provide the effects described herein.

It is appreciated by one of ordinary skill in the art that the scope of the disclosure is not limited to the embodiments set forth herein, and various changes or modifications may be made thereto without departing from the scope and spirit of the disclosure.

Thus, such changes or modifications also belong to the scope of the disclosure defined by the appended claims.

What is claimed is:

1. A device for testing durability of a cowl crossbar, comprising:
    a main picture including an input driver for a rotational durability test and a bending stiffness test on a specimen including motor driven power steering (MDPS)-mounted cowl crossbar, an output loader performing, together with the input driver, the rotational durability test and the bending stiffness test and outputting a test value, and a specimen stand disposed between the input driver and the output loader to relocatably support the specimen; and
    a controller controlling the main picture for the rotational durability test and the bending stiffness test, wherein the input driver includes:
        an input driver motor assembly forming an upper portion of the input driver and connected with the MDPS of the specimen and a steering wheel coupled with the MDPS to control an angle for the rotational durability test and a load for the bending stiffness test; and
        an input driver frame supporting the input driver motor assembly, wherein the input driver, the output loader, and the specimen stand are altogether supported on a base frame.

2. The device of claim 1, wherein for relocating relative to the specimen, the input driver is provided to be relocated by a first ball screw, wherein the output loader is provided to be fixed in position by a U clamp, and wherein the specimen stand is provided to have its height adjusted depending on a position of installation of the specimen.

3. The device of claim 2, wherein the input driver motor assembly is provided to have its height adjusted by a first screw jack, to be moved forward or backward by a second ball screw, and to have its angle adjusted by a second screw jack.

4. The device of claim 3, wherein a first protractor is disposed around the second ball screw and the second screw jack.

5. The device of claim 3, wherein the input driver motor assembly includes:
    a first servomotor for the rotational durability test;
    a first air cylinder for the bending stiffness test;
    a first position detecting module capable of grasping a position of the first air cylinder;
    a first load cell capable of measuring an input load;
    a wheel clamp clamped to or unclamped from the steering wheel; and
    a clamp bar connected with the wheel clamp and the first air cylinder.

6. The device of claim 5, wherein a connector is provided to connect the MDPS to a first serration while controlling an angle of the MDPS by power transferred from the first servomotor through a first decelerator, a first coupling, and a first torque cell to the first serration for the rotational durability test, wherein the input driver frame includes a pneumatic line unit, and wherein the pneumatic line unit controls a load and direction of the first air cylinder using an air pressure.

7. The device of claim 6, wherein the pneumatic line unit includes:
    a direction turning valve supplying air to the first air cylinder and enabling moving forward or backward or stopping;
    an electronic regulator controlling a pressure of the air in a range from 0 Bar to 9 Bar; and
    a manual regulator setting an input air pressure to 6 Bar.

8. The device of claim 6, wherein the output loader includes an output loader motor assembly connected with the MDPS to provide a load, wherein the output loader motor assembly includes a second servomotor for the rotational durability test, and wherein upon the rotational durability test, when a second serration connected with the MDPS is rotated, the second servomotor provides a load in an opposite direction, and the load is measured by a second torque cell between the second serration and the second servomotor and output in a graph.

9. The device of claim 2, wherein a plurality of installation through holes are formed in the base frame to install the input driver, the output loader, and the specimen stand, and wherein the input driver, the output loader, and the specimen stand are installed in predetermined positions on the base frame via the plurality of installation through holes.

10. The device of claim 9, wherein a plurality of anti-slip feet are provided under the base frame, and wherein a cut is formed in a side of the base frame.

11. The device of claim 1, wherein the specimen stand includes:
- a T slot table on which the specimen is mounted;
- a stand screw jack adjusting a height of the T slot table;
- a plurality of specimen supporting jigs provided on the T slot table and supporting the specimen;
- a first side support and a second side support, together with the specimen supporting jigs, supporting the specimen;
- a specimen middle support provided between the first side support and the second side support;
- an upper jig disposed at an upper end of the specimen middle support and supporting the specimen; and
- a plurality of bottom jigs arranged around the specimen middle support and supporting the specimen.

12. The device of claim 11, further comprising a power stopping device operated in association with the controller, wherein the controller controls the power stopping device to automatically stop power when controlling to provide a notification signal to the error lamp and the error buzzer.

13. The device of claim 1, further comprising:
- an error lamp controlled by the controller to visually output an error in a process of testing the durability of the cowl crossbar; and
- an error buzzer controlled to be operated together with the error lamp by the controller and audibly outputting the error.

* * * * *